United States Patent [19]

Andersson et al.

[11] Patent Number: 4,749,780

[45] Date of Patent: Jun. 7, 1988

[54] BIOLOGICALLY ACTIVE FRAGMENTS OF HUMAN ANTIHEMOPHILIC FACTOR AND METHOD FOR PREPARATION THEREOF

[75] Inventors: Lars-Olof Andersson, Knivsta; Nanna Forsman, Järfälla; Kerstin E. I. Larsen, Lidingö; Annelie B. Lundin, Stockholm; Bohdan Pavlu, Huddinge; Inga H. Sandberg, Spånga; Karin M. Sewerin, Bromma, all of Sweden

[73] Assignee: KabiVitrum AB, Stockholm, Sweden

[21] Appl. No.: 835,914

[22] Filed: Mar. 4, 1986

[30] Foreign Application Priority Data

Mar. 5, 1985 [SE] Sweden ............................. 8501050.2

[51] Int. Cl.$^4$ ....................... C07K 15/12; C07K 3/18; C07K 3/22; A61K 37/02
[52] U.S. Cl. .................................... 530/383; 424/101; 530/830
[58] Field of Search ................. 530/383, 830; 424/101

[56] References Cited

U.S. PATENT DOCUMENTS 4,361,509 11/1982 Zimmerman et al. .............. 424/101

FOREIGN PATENT DOCUMENTS 0104356 4/1984 European Pat. Off. .
0123945 11/1984 European Pat. Off. .
0197901 10/1986 European Pat. Off. .

OTHER PUBLICATIONS

Vehar et al., "Structure of Human Factor VIII", *Nature*, vol. 312, Nov. 22, 1984, pp. 337–342.
Wood et al., "Expression of Active Human Factor VIII from Recombinent DNA Clones", Nature, vol. 312, Nov. 22, 1984, pp. 342–347.

*Primary Examiner*—Delbert R. Phillips
*Assistant Examiner*—Nathan M. Nutter
*Attorney, Agent, or Firm*—Pollock, Vande Sande & Priddy

[57] ABSTRACT

Novel, biologically active fragments of human antihemophilic factor, processes for their preparation, pharmaceutical preparations containing them and the use of such fragments in the treatment of patients suffering from hemophilia.

6 Claims, 3 Drawing Sheets

BIOLOGICALLY ACTIVE FRAGMENTS OF HUMAN ANTIHEMOPHILIC FACTOR AND METHOD FOR PREPARATION THEREOF

FIELD OF THE INVENTION

The present invention relates to novel, biologically active fragments of human antihemophilic factor, processes for their preparation, pharmaceutical preparations containing them and the use of such fragments in the treatment of patients suffering from hemophilia.

BACKGROUND OF THE INVENTION

Hemophilia is an inherited disease which has been known for centuries but it is only within the last three decades that it has been possible to differentiate between the various forms; hemophilia A, hemophilia B and hemophilia C. Hemophilia A is the most frequent and affects only males in frequency of one or two individuals per 10,000 males. The disease is caused by strongly decreased level or absence of biologically active coagulation factor VIII or as it also has been called the antihemophilic factor. Factor VIII is a protein normally present in plasma. The clinical manifestation of hemophilia A is a strong bleeding tendency and before treatment with Factor VIII concentrates was introduced the mean age of death of hemophiliacs was less than 20 years. Concentrates of Factor VIII obtained from plasma has been available for treatment of hemophilia A for about two decades. This has improved the situation for hemophilia patients considerably and given most of them possibility to live a normal life. However, there are certain problems with the concentrates and their use. The concentrates presently available are rather impure having a specific activity of less than 2 units Factor VIII/mg protein and containing <1% of Factor VIII protein. Further they are fairly expensive because the starting material, plasma, is expensive and the yields in the purification processes used are low with the low purity products. There is also the risk for transmittance of hepatitis B virus and other infective agents. Finally, about one tenth of the patients with severe hemophilia A do develop antibodies against Factor VIII and then become very difficult to treat as the injected Factor VIII is neutralized and inhibited by the antibodies.

There is a need for highly purified Factor VIII-containing preparations. The present specification describes such highly purified preparations. The invention also provides novel, defined fragments of Factor VIII which have improved properties compared to existing Factor VIII preparations in particular higher specific activity and longer half-life in blood. Clinical use of purified, biologically active fragments of Factor VIII can give certain advantages compared to presently used Factor VIII concentrates. The high degree of purification is an advantage as very little contamination proteins then are given to the patient and further, and more important, the risk for hepatitis B transmission is strongly diminished. A longer half-life is a great advatage as a prolonged action is obtained and thereby smaller amounts need to be given. Further for the hemophilia A patients who have developed or are at risk for developing antibodies against Factor VIII it is probably an advantage to give a smaller part of the Factor VIII molecule as it is likely to be less challenging for the immune system.

As was reported recently (J. Gitschier et al. Nature 312, 330-337, 1984, J. Toole et al. Nature 312, 342-347, 1984), intact Factor VIII can be made in cell culture using recombinant DNA techniques. An additional advantage with active fragments of Factor VIII is that such fragments can probably be made more easily and efficiently by the recombinant DNA cell culture techniques than the whole Factor VIII molecule as they are smaller and can therefore be regarded as especially advantageous to produce by this technique.

Prior art

Many attempts have been made to purify human Factor VIII. Presently, however, no one has succeeded to isolate a defined single protein component with Factor VIII activity. Commercial Factor VIII concentrates have been used as starting material, where the Factor VIII is present as a complex with another protein, the von Willebrand Factor. The techniques used that have produced the purest Factor VIII products are immunoadsorbent chromatography with matrix bound antibodies against von Willebrand Factor combined with chromatography on aminohexyl-agarose (C. A. Fulcner and T. S. Zimmerman, Proc.Natl.Acad.Sci. 79, 1648-1652, 1982. T. S. Zimmerman and C. A. Fulcher, EP 0123945, 1984) and chromatography on agarose in the presence of $CaCl_2$ to dissociate Factor VIII from von Willebrand Factor combined with chromatography on QAE cellulose (P. J. Fay et al., Proc.Natl.Acad.Sci. 79, 7200-7204, 1982. S. I. Chavin and P. J. Fay, EP 0104356, 1984). Fulcher and Zimmerman obtained a Factor VIII material of a specific activity of 2,294 units/mg which contained a number of components as shown by sodium dodecyl sulfate polyacrylamide electrophoresis. The majority and the most dominant of the components had molecular weights below 92,000 daltons. However, their data did not show which peptide(s) of which combination of peptides that was necessary for activity. Fay et al. described a Factor VIII product with the specific activity, 4,900 units/mg and that the material migrated as a single major component of 100,000 daltons in sodium dodecyl sulfate polyacrylamide electrophoresis in reducing media. However, fainter bands were also seen at >220,000 daltons. The different results obtained by different groups demonstrate the large uncertainty concerning the biochemical character of Factor VIII. Recently the human Factor VIII gene has been characterized and human Factor VIII activity has been expressed by recombinant DNA technique. (J. Gitschier et al., Nature 312, 330-337, 1984, J. Toole et al., Nature 312, 337-347, 1984). The nucleotide sequence data on the gene indicates that intact Factor VIII has a molecular weight around 300,000 daltons.

DETAILED DESCRIPTION OF THE INVENTION

In the following specification a number of abbreviations, product designations and assay methods are mentioned. The following list indicates such terms and an explanation thereof:

Abbrevations

Diisopropylflourphosphate—DFP
Ethylenedinitrotetraaceticacid—EDTA.
Factor VIII coagulant activity—VIII:C
Factor VIII coagulant antigen—VIIIC:ag
Factor VIII related antigen—VIIIR:Ag
High performance liquid chromatography—HPLC
Sodium dodecyl sulfate polyacrylamide electrophoresis—SDS-PAGE
Trichloroaceticacid—TCA

Product designations

Mono Q gel—an anion-exchanger from Pharmacia composed of a hydrophilic polymer with the ionic groups—$CH_2N^+(CH_3)_3$ Octonativ ®—a commercial high purity Factor VIII concentrate from KabiVitrum AB produced from cryoprecipitate by affinity chromatography.

TSK DEAE 5 PW—an anion exchanger from Toyosoda composed of a hydrophilic polymer with the ionic groups—$CH_2CH_2N^+(CH_2CH_3)_2$ TSK 4,000 SW—a silicabased gel with a hydrophilic surface functionality of OH groups for size exclusion chromatography, obtained from Toyosoda.

Assays

Factor VIII coagulant activity:

Factor VIII coagulant activity (VIII:C) was usually measured by a one stage clotting assay. (M. Mikaelsson and U. Oswaldsson. Standardization of VIII:C assays: A manufacturer's view. In: Factor VIII concentrates and their clotting activity. I. M. Nilsson, T. W. Barrowcliffe and K. Schimpf (eds.). Scand.J.Haematol.Suppl. 33, 79–86, 1984). As substrate plasma was used an artificial FVIII:C deficient reagent (D. Nyman, Thromb.Diath. Haemorrh.23, 306–311, 1979). Sample and calcium chloride solution are added at the same time to a preincubated mixture of VIII:C deficient plasma, ellagic acid and phospholipid. A semiautomatic coagulometer (LODE) was used to determine the clotting time.

VIII:C in plasma samples from hemphilia dogs was determined with a chromogenic method for VIII:C described by S. Rosen, U. Oswaldsson, M. Blombäck, M. Larrieu, I. M. Nilsson and H. Vinazzer. Scand. J. Haematol. 331, Suppl. 40, 139–145, 1984.

Factor VIII coagulant antigen:

The factor VIII coagulant antigen (VIIIC:Ag) was determined with a solid phase immunoradiometric assay (L. Holmberg, L. Borge, R. Ljung and I. M. Nilsson. Scand.J.Haematol. 23, 17–24, 1979). The antibody was kindly provided by Prof. I. M. Nilsson, Malmö, Sweden.

von Willebrand Factor:

von Willebrand Factor or factor VIII related antigen (VIIIR:Ag) was measured with a quantitative electroimmunoassay (C. B. Laurell, Scand.J.Clin.Lab.Invest. 29, (Suppl. 124), 21–37, 1972. Goat antiserum from Atlantic antibodies was used. The VIIIR:Ag assays were standardized against the First British Standard for Blood Coagulation Factor VIII related Antigen Human for Immunoassay (66/355).

Sodium dodecyl sulfate polyacrylamide gel electrophoresis: Sodium dodecyl sulfate polyacrylamide gel electrophoresis (SDS-PAGE) was performed according to Laemmli employing a stacking gel of T=4% (total polyacrylamide concentration) and a separating gel of T=6% or 7.5%. In all cases crosslinkage degree was 3.3%. Samples were treated with 5% mercaptoethanol and 2% sodium dodecyl sulfate. Electrophoresis was at 20 mA for four hours. Gels were stained for protein using a silver staining technique described by Tunon and Johansson. (U.K. Laemmli.Nature 227, 680685, 1970. P. Tunon and K. E. Johansson. J.Biochem.Biophys. Methods 9, 171–179, 1984).

Protein estimation

The protein of the VIII:C material obtained in the Mono-Q gel step was quantitated by aminoacid analysis. Hydrolysis with 6 N HCl was carried out for 22 hours at 110° C. in evacuated glass tubes. The hydrolysate was assayed with a Beckman 121M analyzer.

The present specification describes a novel method for obtaining a Factor VIII preparation which has higher specific activity than previously described Factor VIII preparations. The novel purification method comprises the use of immunoaffinity chromatography followed by HPLC on an anion-exchange adsorbent. The purified Factor VIII preparation obtained is a suitable starting material to obtain the novel Factor VIII fragments according to the invention.

It has been found according to the invention that the purified material contains several different peptide chains as shown by SDS-PAGE, most of them of higher molecular weight than has been previously reported. The peptides have been separated, characterized and defined. The data show that all peptides are related to Factor VIII and that certain combinations of peptides are necessary for factor VIII activity. These novel peptides constitute part of the invention.

As starting material for the Factor VIII purification procedure is used a solution of high purity Factor VIII concentrate. One such suitable concentrate is Octonativ ®. The first step in the purification is the adsorption of the Factor VIII-von Willebrand Factor complex present in the Factor VIII concentrate to a column containing antibodies against von Willebrand Factor covalently coupled to a gel matrix such as agarose. Preferably polyclonal antibodies are used but also monoclonal antibodies can be used. Most other proteins present in the solution just pass through this column. Factor VIII is then dissociated from the von Willebrand Factor and eluted off the column by allowing a solution containing $Ca^{2+}$ or $Na^+$ ions to pass through the column. The concentration of $Ca^{2+}$ or $Na^+$ ions is chosen so that Factor VIII is dissociated from the von Willebrand Factor and eluted. Suitable concentration ranges for $Ca^{2+}$ are 0.15–1.0 M, preferably 0.2–0.5 M. Suitable concentration ranges for $Na^+$ are 0.5–2.0 M, suitably 1.0 M. It is prefered to use calcium ions. Suitably $CaCl_2$ or NaCl is used. The Factor VIII material eluted is very much purified compared to the starting material but is still not pure. Final purification is obtained by HPLC at pH 6–8 on an anion-exchange adsorbent such as Mono Q gel (Pharmacia) or TSK DEAE 5 PW gel (Toyosoda). The Factor VIII material is eluted in a sodium chloride or calcium chloride salt gradient. This material has a specific activity of 5,000–9,000 units/mg protein and thus a 360,000–640,000 fold purification from plasma has been obtained. The material obtained at the purification procedure described above contained both intact and partly fragmented forms of Factor VIII.

In order to obtain Factor VIII fragments, the purified material of the partly purified material was incubated with a very low concentration ($10^3$-NIH units/unit of Factor VIII) of the coagulation enzyme thrombin suitably at 37° C. for 10–300 minutes, preferably 60–90 minutes. After this treatment most of Factor VIII activity appeared later in the HPLC-elution curve corresponding to what was called Factor VIII active peak 11, see FIG. 3. Analysis of this material by SDS-PAGE in reducing media showed the presence of two peptide chains with molecular weights 90,000 and 80,000 daltons.

Generation of Factor VIII fragments could also be accomplished in a simpler but less controlled way by allowing a solution of partly purified Factor VIII containing added $Ca^{2+}$ ions to stand at 4°–37° C. for more than one hour and up to about 24 hours. The trace amounts of thrombin or possibly other proteases present such as kallikrein, was sufficient to cause fragmentation under those conditions. Separation of this material by HPLC on an anion exchanger showed two main Factor VIII active areas, peak I and II, see FIG. 3. Peak I was not a single peak but contained four or five partly resolved peaks. Analysis of the various subfractions by SDS-PAGE in reducing media showed that all contained a 80,000 dalton molecular weight peptide and in addition in first front fraction a peptide of molecular weight 180,000 daltons, in front and middle fractions peptides of molecular weight 160,000 and 150,000 daltons and in rear fractions peptides of molecular weight 130,000 and 115,000 daltons. Further resolution of components was accomplished by HPLC gel filtration on TSK 4000 SW of the subfractions of peak 1. The main components of the various subfractions were all shown to have Factor VIII activity. The peak 11 material contained only two peptide chains of molecular weights 90,000 daltons and 80,000 daltons. HPLC gel filtration on TSK 4000 SW of the peak I and 11 material in the presence of EDTA to bind metal ions resulted in loss of activity and in dissociation of the 180,000, 160,000, 150,000, 130,000 and the 115,000 dalton peptides from the 80,000 dalton peptide in peak I and the dissociation of the 90,000 dalton peptide from the 80,000 dalton peptide in peak II. This indicates that the Factor VIII peptides are held together by one or several metal ion bridges.

An alternative method for obtaining the novel Factor VIII fragments of the invention comprises separating a fragmented Factor VIII containing material using a gel matrix containing antibodies against von Willebrand Factor as described above.

In conclusion fragmentation of Factor VIII by small amounts of thrombin or by trace amounts of other proteases results in formation of the following six active novel fragments; one composed of a 180,000 daltons and a 80,000 daltons peptide chain, one composed of a 160,000 daltons and a 80,000 daltons peptide chain, one composed of a 150,000 daltons and a 80,000 daltons peptide chain, one composed of a 130,000 daltons and a 80,000 daltons peptide chain, one composed of a 115,000 daltons and a 80,000 daltons peptide chain and one composed of a 90,000 daltons and a 80,000 daltons peptide chain. The two chains in the various fragments are probably held together by metal ion bridges. Thus, each fragment comprises a pair of two peptide chains.

Characterization of the various peptide chains was performed using aminoacid analysis, aminoterminal aminoacid sequence determination and immunological techniques. The data obtained showed that the 180,000, 160,000, 150,000, 130,000, 115,000 and the 90,000 daltons peptide chains all had the same aminoterminal amino acid sequence Ala-Thr-Arg-Arg-Tyr-Tyr-. The 80,000 dalton peptides present in active components all showed the same aminoterminal sequence Glu-Ile-Thr-Arg-Thr-Thr-, thus it is the same peptide in the various components. This was also confirmed by immunological studies.

To study if the various fragments of Factor VIII also had in vivo antihemophilic activity a series of experiments were performed where hemophilia dogs were infused with the various preparations and the hemostatic effect and half-life of antihemophilic activity were followed. Surprisingly it was found that all the fragments had in vivo antihemophilic activity and a half-life comparable to Factor VIII and for the smallest fragment, the peak II material, the half-life was longer. Thus certain fragments of Factor VIII containing as little as two third of the intact Factor VIII molecule can have full in vivo antihemophilic activity and normal or even prolonged half-life. Previously it has not been known that it was possible to get full biological activity and normal or prolonged half-life in the circulation with less than the whole Factor VIII molecule. It is well established however that activation of Factor VIII can occur upon exposure to activated Factor X or thrombin. In contrast to what is the case with fragmented Factor VIII molecules described in this invention the activated Factor VIII has very short half-life and its composition is not presently known with certainty.

Example 1 Preparation of Purified Factor VIII

Figure 1:
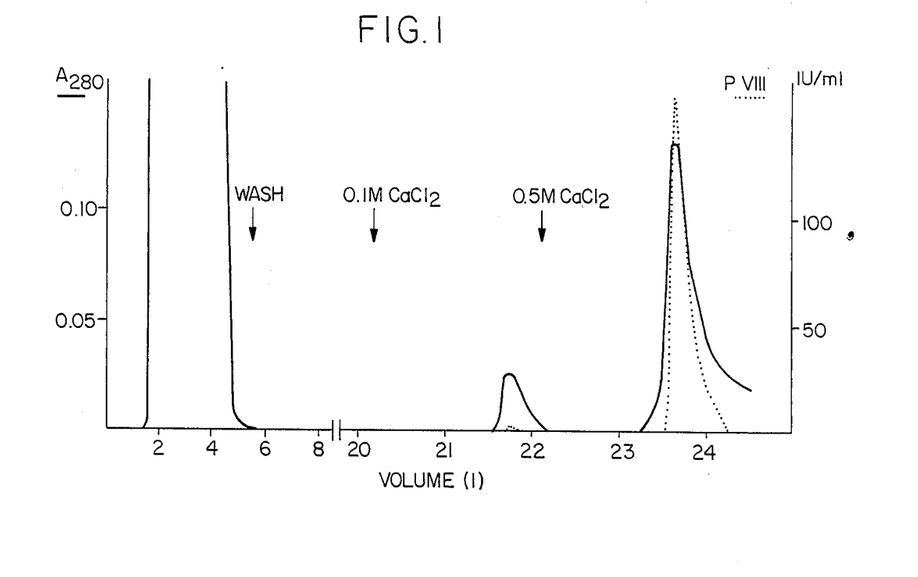
FIG. 1 illustrates immunoaffinity chromatography of a Factor VIII-von Willebrand complex.

A commercial high purity Factor VIII concentrate, Octonativ ® (KabiVitrum AB) was dissolved in sterile water containing 1 mM DFP. The amount of Octonativ ® dissolved corresponded to 60,600 units of Factor VIII activity. The solution was applied to a column containing polyclonal goat antibodies against von Willebrand Factor coupled to Sepharose CL-2B gel. The amount of antibody coupled was about 6 mg IgG/ml gel. The column was then washed with 0.05 M sodium acetate, 0.15 M NaCl, 1 mM DFP buffer pH 7.3 followed by 0.05 M Tris, 0.15 M NaCl, 2 mM $CaCl_2$ buffer pH 7.35 and finally with 0.05 M Tris, 0.15 M NaCl, 0.1 M $CaCl_2$ buffer pH 7.35. Elution of Factor VIII was accomplished by applying a 0.05 M Tris, 0.15 M NaCl buffer pH 7.35 containing 0.5 M $CaCl_2$. The elution diagram is shown in FIG. 1. The Factor VIII containing eluate was then concentrated about 40 times in an Amicon cell with a Diaflo PM 10 membrane and the buffer was exchanged to 0.02 M Tris, 0.05 M $CaCl_2$ buffer pH 6.8 using a Sephadex G-25 column. This solution was subjected to HPLC using Mono-Q as ionexchange adsorbent. Elution was performed using a salt gradient from 0 to 1.5 M NaCl.

The Factor VIII activity eluted late (peak I position) as one broad peak. Table I gives an overview of the purification process.

TABLE I

Scheme over purification of Factor VIII from Octonativ<sup>R</sup>.

| Purification step | Protein (mg) tot | VIII:C tot (IU) | VIIIC:Ag tot (U) | VIIIR:Ag tot (U) | VIII:C (IU) protein (mg) | VIII:C yield (%) |
|---|---|---|---|---|---|---|
| Octonativ | 74,624 | 60,670 | 69,426 | 279,825 | 1.23 | 100 |
| anti-vWF-eluate | 43.4 | 24,680 | 29,311 | 0 | 569 | 41 |
| Mono-Q gel eluate | 1.6 | 10,391 | 10,074 | 0 | 6,494 | 17 |

Example 2 Preparation of fragments of Factor VIII

Figure 2:
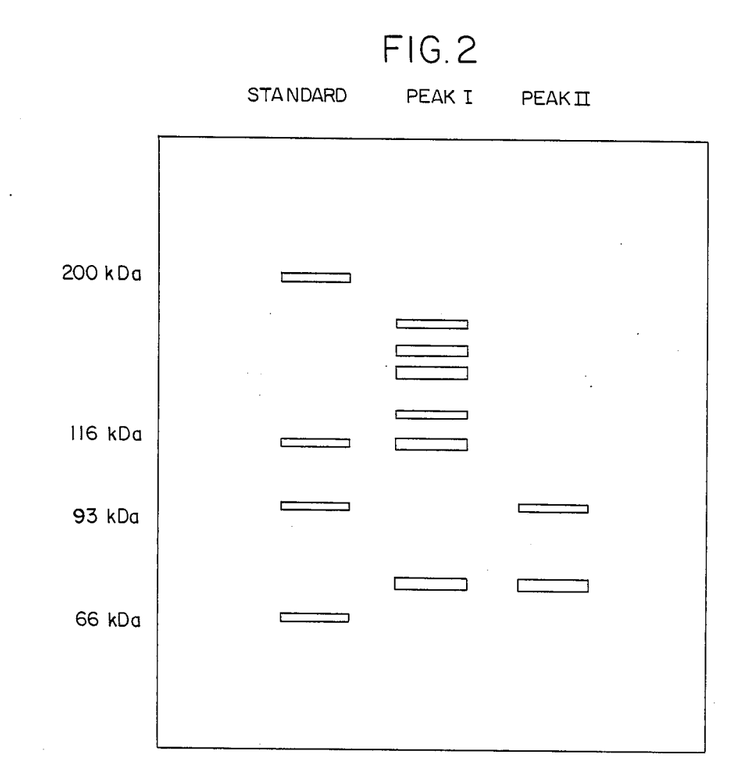
FIG. 2 shows gel electrophoresis of a Factor VIII eluate.

The material obtained in Example 1 was dialyzed against 0.02 M Tris, 2 mM $CaCl_2$ buffer pH 6.8 and purified human thrombin (specific activity 2,800 units/mg) was added to a final concentration of $10^{-3}$ NIH units per unit of Factor VIII. After 60 minutes of incubation at 37° C. the reaction was stopped by adding the thrombin inhibitor I-2581 and the material was subjected to high pressure liquid chromatography on Mono-Q gel using salt gradient elution as before. Now the main part of Factor VIII active material eluted later than before (peak II) position). The specific activity of this material was 7,300 units/mg protein and SDS-PAGE in the presence of mercaptoethanol showed it to contain two main components see FIG. 2, one peptide chain of molecular weight 90,000 daltons and another of molecular weight 80,000 daltons. Elution of material from the polyacrylamide gels could be accomplished and the aminoacid composition as well as the aminoterminal aminoacid sequence of the two peptides was determined. The aminoacid composition is given in Table 11 of Example 3. Aminoterminal aminoacid sequence was determined using a gas phase sequenator. The 90,000 dalton peptide chain had the aminoterminal aminoacid sequence Ala-Thr-Arg-Arg-Tyr-Tyr- and the 80,000 daltons peptide chain Glu-Ile-Thr-Arg-Thr-Thr-.

The Factor VIII activity of the material eluted from Mono-Q gel could be inhibited by addition of antibodies against Factor VIII obtained from a hemophilia patient as well as by a monoclonal antibody prepared by immunization of mice with purified Factor VIII. Immunoblotting of the separated peptide chains showed that the antibodies from the hemophilia patient and the monoclonal antibodies reacted with the 80,000 dalton chain.

Example 3 Preparation of Factor VIII fragments

Figure 3:
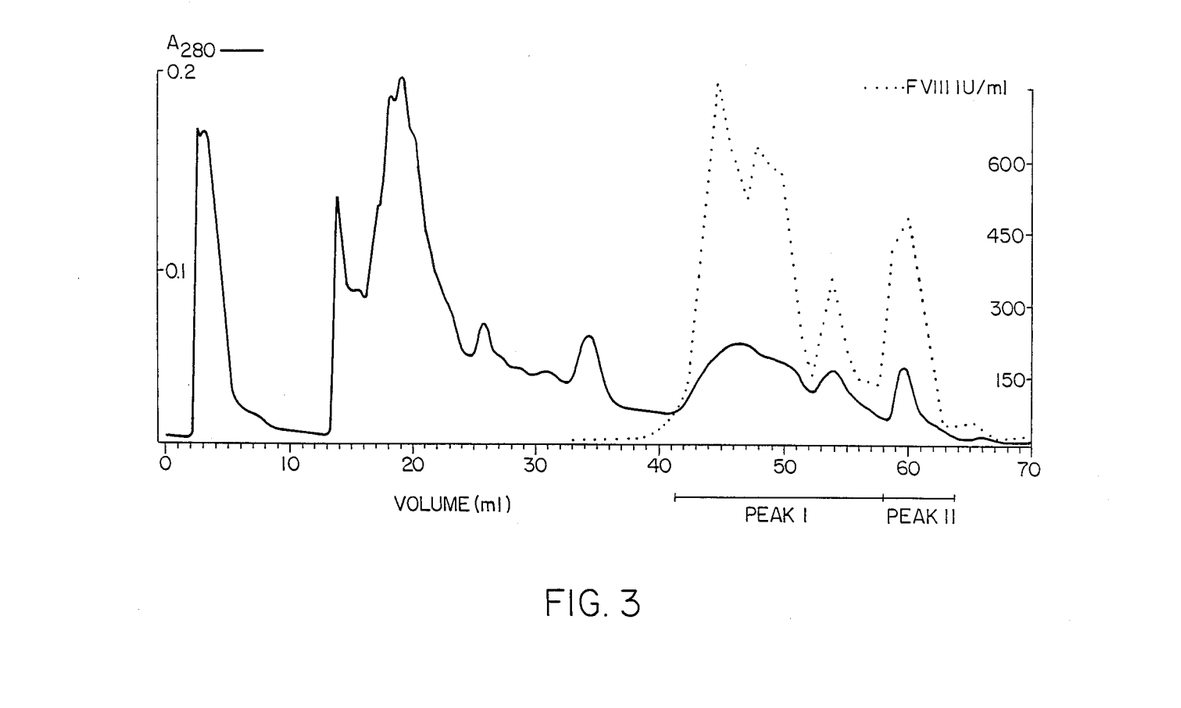
FIG. 3 is a chromatograph of a Factor VIII containing eluate.

A commercial high purity Factor VIII concentrate, Octonativ® (KabiVitrum AB) corresponding to 67,000 units Factor VIII was dissolved in sterile water containing 1 mM DFP. The solution was applied to a column containing polyclonal goat antibodies against von Willebrand Factor coupled to Sepharose CL-2B gel. The column was washed and the Factor VIII activity fraction eluted as described in Example 1. The Factor VIII containing eluate was concentrated about 45 times in an Amicon cell with a Diaflo PM 10 membrane and the buffer was exchanged to 0.02 M Tris, 0.05 M $CaCl_2$ buffer pH 6.8 on a Sephades G-25 column. This solution was allowed to stand at 8° C. for 18 hours and was then subjected to HPLC on Mono-Q adsorbent as described in Example 1. The elution diagram obtained is illustrated in FIG. 3. Here two main peaks of Factor VIII activity are found, peak I and 11. Peak I is not homogenous but probably contains four or five partly resolved components. To study this, peak I was divided into five fractions and each fraction was subjected to HPLC gel filtration on TSK 4000 SW. One main component having Factor VIII activity was obtained in all fractions but the molecular sizes as apparent from the elution position were slightly different. SDS-PAGE in the presence of mercaptoethanol of the peak fractions showed that fraction 1 mainly contained two components, one of molecular weight 180,000 daltons and the other 80,000 daltons. Fraction 2 contained mainly two components of molecular weights 160,000 and 80,000 daltons, respectively. Fraction 3 contained mainly two components of molecular weights 150,000 and 80,000 daltons, respectively. Fraction 4 contained mainly two components of molecular weights 130,000 and 80,000 daltons, respectively. Fraction 5 contained mainly two components of molecular weights 115,000 and 80,000 respectively. Elution of material from the polyacrylamide gels could be accomplished and the aminoacid composition a well as the aminoterminal aminoacid sequence was determined. The aminoacid composition is given in Table 11. The 180,000, 160,000, 150,000, 130,000 and 115,000 daltons peptides all had the same aminoterminal sequence Ala-Thr-Arg-Arg-Tyr-Tyr-. The 80,000 daltons peptide chain had the aminoterminal sequence Glu-Ile-Thr-Arg-Thr-Thr-. Peak 11 was analyzed by SDS-PAGE in the presence of mercaptoethanol and shown to contain two peptide chains of molecular weights 90,000 and respectively. Aminoacid analysis and aminoterminal sequence determination showed to be identical to the peptides described in example 1.

The Factor VIII activity of all the various fractions could be inhibited by addition of antibodies against Factor VIII obtained from a hemophilia patient as well as by a monoclonal antibody prepared by immunization of mice with purified Factor VIII. Immunoblotting showed that both antibodies reacted with the 80,000 daltons peptide chain in all of the fractions.

The aminoacid composition of the various fractions is given in Table 11 (molar percentages):

TABLE II

Aminoacid composition of the various peptide chains of Factor VIII:

|  | 180 kD | 160 kD | 150 kD | 130 kD | 115 kD | 90 kD | 80 kD |
|---|---|---|---|---|---|---|---|
| Cys | 0.8 | 0.8 | 0.8 | 1.0 | 1.1 | 1.4 | 1.3 |
| Asp | 5.7 | 5.8 | 6.0 | 6.5 | 6.7 | 6.8 | 4.7 |
| Asn | 5.8 | 5.9 | 5.7 | 5.0 | 4.5 | 4.2 | 4.5 |
| Thr | 6.6 | 6.5 | 6.2 | 6.3 | 6.2 | 5.3 | 6.1 |
| Ser | 10.0 | 9.6 | 9.7 | 10.0 | 9.4 | 7.8 | 8.3 |
| Glu | 6.2 | 6.3 | 6.3 | 5.9 | 5.8 | 6.1 | 5.7 |
| Gln | 4.2 | 4.0 | 3.8 | 3.3 | 3.5 | 3.2 | 5.7 |
| Pro | 5.7 | 5.5 | 5.8 | 5.8 | 6.1 | 5.4 | 4.5 |
| Gly | 5.3 | 5.6 | 5.6 | 5.6 | 5.6 | 5.8 | 5.7 |
| Ala | 4.5 | 4.4 | 4.4 | 4.6 | 4.8 | 5.0 | 4.8 |
| Val | 5.3 | 5.5 | 5.7 | 5.5 | 5.8 | 6.8 | 5.4 |
| Met | 2.4 | 2.6 | 2.7 | 2.6 | 2.6 | 2.6 | 3.5 |
| Ile | 4.4 | 4.1 | 4.3 | 4.4 | 4.4 | 4.7 | 5.7 |
| Leu | 10.0 | 10.0 | 10.1 | 10.3 | 9.9 | 9.6 | 7.7 |
| Tyr | 3.2 | 3.3 | 3.3 | 3.8 | 4.3 | 5.1 | 4.4 |
| Phe | 4.4 | 4.5 | 4.4 | 4.5 | 4.7 | 4.9 | 5.7 |
| Trp | 1.2 | 1.3 | 1.4 | 1.5 | 1.5 | 1.8 | 2.2 |
| Lys | 6.9 | 6.8 | 6.6 | 5.9 | 5.4 | 5.5 | 5.4 |

TABLE II-continued

Aminoacid composition of the various peptide chains of Factor VIII:

| | 180 kD | 160 kD | 150 kD | 130 kD | 115 kD | 90 kD | 80 kD |
|---|---|---|---|---|---|---|---|
| His | 3.2 | 3.2 | 3.3 | 3.3 | 3.4 | 3.4 | 3.5 |
| Arg | 4.3 | 4.2 | 4.0 | 4.3 | 4.4 | 4.7 | 5.0 |

Biological tests

A. In vivo survival of purified Factor VIII in normal dogs

In vivo survival of the purified Factor VIII fractions described in Examples 2 and 3 was studied using normal dogs.

For studies in normal dogs the peak I and peak II material from the Mono-Q gel step was labelled with $^{125}I$ using the Iodogen method. The labelled protein was separated from non-covalently bound iodine using gel filtration on Sephadex G-25. The specific activity was 5.3 µCi/µg and 3.8 µCi/µg for peak I and II, respectively. The Factor VIII labelled by this method retained 50-100% of its clotting activity. SDS-PAGE in the presence of mercaptoethanol showed that it had identical electrophoretic properties as unlabelled material.

Three dogs each received an intravenous injection of 4 µg $^{125}I$-labelled peak I material (~20 µCi). One of the dogs also received a tenfold excess (~40 µg) of unlabelled Factor VIII in order to study a possible dose-dependent plasma elimination. After three weeks when the plasma radioactivity had returned to base line levels two of the dogs received an additional injection of 4 µg (~15 µCi) $^{125}I$-labelled peak II material. Blood samples of 2 ml were collected at certain time intervals (from 1 minute to 56 hours) using Venoject vacutainer tubes containing 0.2 ml 0.13 M sodium citrate. The blood samples were immediately counted for radioactivity.

The degradation rate of the $^{125}I$-Factor VIII to metabolites and free iodine was analyzed by gel filtration of plasma collected at 1.5, 26 and 51 hours after the injection, on a Sephadex G-25 column. This was also analyzed by precipitation of plasma with TCA. Plasma, 1 ml, was precipitated with 1 ml 20% TCA. After centrifugation for 10 min at 1,500 g the radioactivity was counted in precipitate and supernatant.

Figure 4:
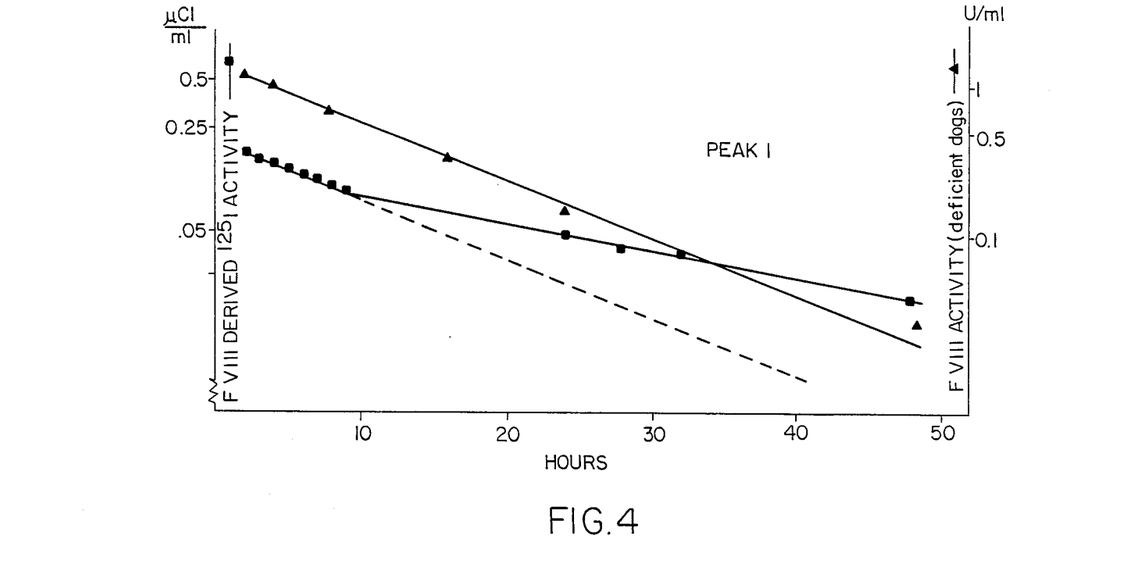
FIGS. 4 and 5 plot bioexponential decline of radioactivity in blood from dogs receiving Factor VIII fragments of the present invention.
Figure 5:
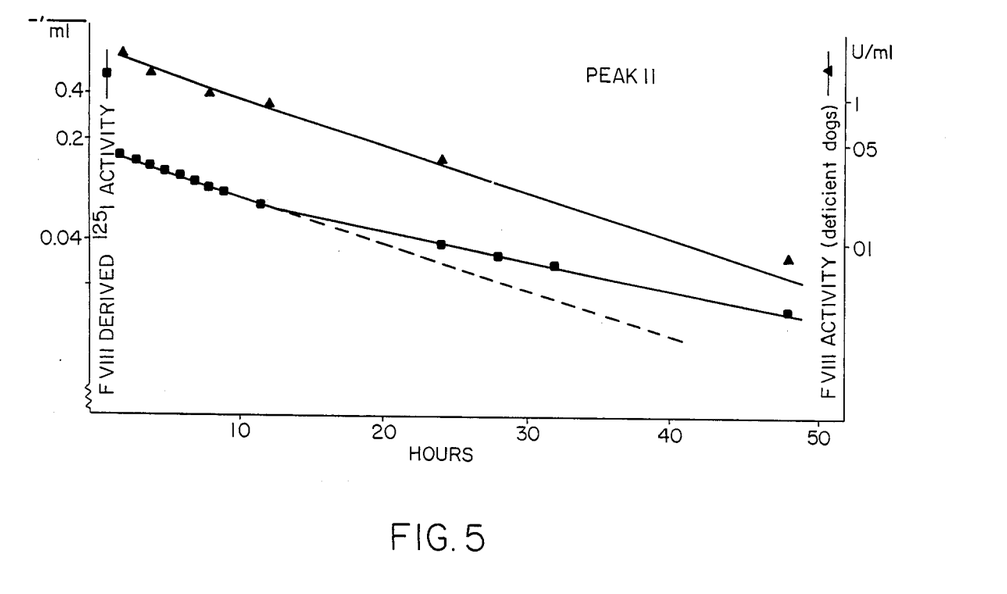

The results showed that the Factor VIII bound $^{125}I$-radioactivity was eliminated with a half-life of 7.6 hours±0.2 (n=3) and 10.0 hours±0.2 (n=2) for peak I and II, respectively. The bioexponential decline of radiolabelled peak I and II material is shown in FIG. 4 and FIG. 5.

B. Hemostatic effect and in vivo survival in hemophilia dogs

The hemostatic effect of the Factor VIII fractions was tested in hemophilia A dogs using the model described by A.R. Giles, S. Tinlin and R. Greenwood, (Blood 60, 727-730, 1982). Bleeding was induced in lightly anesthetized animals by severing the apex of the nail cuticle using a guillotine device. In the normal dog bleeding ceased after 2-8 min if the clot was not disturbed. However, the hemophilic animal showed a quite different pattern. Bleeding occasionally stopped spontaneously within the same time interval as noted for normal dogs but it always restarted and continued until measures were taken by the operator to arrest the bleeding.

Two hemophilia A dogs which were severely Factor VIII deficient (<1% Factor VIII of normal level) were used in the study and received intravenous injections of peak I and II material, respectively, obtained accordning to Examples 2 and 3. The amount of Factor VIII injected was calculated to be sufficient to give an initial plasma level of 2 units Factor VIII activity/ml (200% of the normal human level). Blood samples of 5 ml were collected at time intervals from 2 min to 96 hours after injection. The samples were immediately centrifuged at 2,000 g for 20 min to obtain platelet poor plasma. The plasma was assayed for Factor VIII.

Both dogs bled vigorously from their clipped toenails before injection of the material. The dog which recieved peak II material had also developed a spontaneous and fatal bleeding at the root of its tongue prior to injection. About thirty minutes following injection the bleeding from the cuticle of the dog given peak I material was completely arrested. The bleedingtime was corrected to within the normal range as tested after disturbance of the clot. A similar hemostatic effect was obtained in the dog given peak II material. The bleeding from the cuticle as well as from the tongue stopped completely within thirty minutes after injection. A normal bleedingtime was then recorded. The in vivo survival of the biological activity was measured with the chromogenic assay for Factor VIII. The results showed that the Factor VIII declined with a half-life of 7.0 and 10.0 hours for peak I and 11, respectively. These results were thus in accordance with those obtained with $^{125}I$-labelled Factor VIII in normal dogs. The bioexponential decline of activity after injection of peak I and peak II material is shown in FIG. 4 and FIG. 5. In vivo recovery of injected Factor VIII fragments was between 90 and 100 percent.

In clinical practice the novel Factor VIII fragments of the invention can be administered and used for the same indication where high purity Factor VIII preparations are normally used. The amount to be administered will depend on the needs of the individual patient to normalize hemostatis.

We claim:

1. Active fragment of human Factor VIII characterized by containing two peptide chains having molecular weights 90,000 daltons and 80,000 daltons, respectively and having the aminoterminal amino acid sequences Ala-Thr-Arg-Arg-Tyr-Tyr- and Glu-Ile-Arg-Thr-Thr-, respectively and having the aminoacid composition:

| | 90 kD | 80 kD |
|---|---|---|
| Cys | 1.4 | 1.3 |
| Asp | 6.8 | 4.7 |
| Asn | 4.2 | 4.5 |
| Thr | 5.3 | 6.1 |
| Ser | 7.8 | 8.3 |
| Glu | 6.1 | 5.7 |
| Gln | 3.2 | 5.7 |
| Pro | 5.4 | 4.5 |
| Gly | 5.8 | 5.7 |
| Ala | 5.0 | 4.8 |
| Val | 6.8 | 5.4 |
| Met | 2.6 | 3.5 |
| Ile | 4.7 | 5.7 |
| Leu | 9.6 | 7.7 |
| Tyr | 5.1 | 4.4 |
| Phe | 4.9 | 5.7 |
| Trp | 1.8 | 2.2 |
| Lys | 5.5 | 5.4 |

|  | 90 kD | 80 kD |
|---|---|---|
| His | 3.4 | 3.5 |
| Arg | 4.7 | 5.0 |

2. Active fragment of human Factor VIII characterized by containing two peptide chains having molecular weight 115,000 daltons and 80,000 daltons, respectively and having the aminoterminal sequences Ala-Thr-Arg-Arg-Tyr-Tyr- and Glu-Ile-Thr-Arg-Thr-Thr-, respectively and having the aminoacid composition:

|  | 80 kD | 115 kD |
|---|---|---|
| Cys | 1.3 | 1.1 |
| Asp | 4.7 | 6.7 |
| Asn | 4.5 | 4.5 |
| Thr | 6.1 | 6.2 |
| Ser | 8.3 | 9.4 |
| Glu | 5.7 | 5.8 |
| Gln | 5.7 | 3.5 |
| Pro | 4.5 | 6.1 |
| Gly | 5.7 | 5.6 |
| Ala | 4.8 | 4.8 |
| Val | 5.4 | 5.8 |
| Met | 3.5 | 2.6 |
| Ile | 5.7 | 4.4 |
| Leu | 7.7 | 9.9 |
| Tyr | 4.4 | 4.3 |
| Phe | 5.7 | 4.7 |
| Trp | 2.2 | 1.5 |
| Lys | 5.4 | 5.4 |
| His | 3.5 | 3.4 |
| Arg | 5.0 | 4.4 |

3. Active fragment of human Factor VIII characterized by containing two peptide chains having molecular weight 130,000 daltons and 80,000 daltons, respectively and having the aminoterminal aminoacid sequences Ala-Thr-Arg-Arg-Tyr-Tyr- and Glu-Ile-Arg-Thr-Thr-, respectively and the aminoacid composition:

|  | 80 kD | 130 kD |
|---|---|---|
| Cys | 1.3 | 1.0 |
| Asp | 4.7 | 6.5 |
| Asn | 4.5 | 5.0 |
| Thr | 6.1 | 6.3 |
| Ser | 8.3 | 10.0 |
| Glu | 5.7 | 5.9 |
| Gln | 5.7 | 3.3 |
| Pro | 4.5 | 5.8 |
| Gly | 5.7 | 5.6 |
| Ala | 4.8 | 4.6 |
| Val | 5.4 | 5.5 |
| Met | 3.5 | 2.6 |
| Ile | 5.7 | 4.4 |
| Leu | 7.7 | 10.3 |
| Tyr | 4.4 | 3.8 |
| Phe | 5.7 | 4.5 |
| Trp | 2.2 | 1.5 |
| Lys | 5.4 | 5.9 |
| His | 3.5 | 3.3 |
| Arg | 5.0 | 4.3 |

4. Active fragment of human Factor VIII characterized by containing two peptide chains having molecular weights 150,000 daltons and 80,000 daltons, respectively, and having the aminoterminal sequences Ala-Thr-Arg-Arg-Tyr-Tyr- and Glu-Ile-Arg-Thr-Thr-, respectively, and the aminoacid composition:

|  | 80 kD | 150 kD |
|---|---|---|
| Cys | 1.3 | 0.8 |
| Asp | 4.7 | 6.0 |
| Asn | 4.5 | 5.7 |
| Thr | 6.1 | 6.2 |
| Ser | 8.3 | 9.7 |
| Glu | 5.7 | 6.3 |
| Gln | 5.7 | 3.8 |
| Pro | 4.5 | 5.8 |
| Gly | 5.7 | 5.6 |
| Ala | 4.8 | 4.4 |
| Val | 5.4 | 5.7 |
| Met | 3.5 | 2.7 |
| Ile | 5.7 | 4.3 |
| Leu | 7.7 | 10.1 |
| Tyr | 4.4 | 3.3 |
| Phe | 5.7 | 4.4 |
| Trp | 2.2 | 1.4 |
| Lys | 5.4 | 6.6 |
| His | 3.5 | 3.3 |
| Arg | 5.0 | 4.0 |

5. Active fragment of human Factor VIII characterized by containing two peptide chains having molecular weights 160,000 daltons and 80,000 daltons, respectively, and having the aminoterminal sequences Ala-Thr-Arg-Arg-Tyr-Tyr- and Glu-Ile-Thr-Arg-Thr-Thr-, respectively, and the aminoacid composition:

|  | 80 kD | 160 kD |
|---|---|---|
| Cys | 1.3 | 0.8 |
| Asp | 4.7 | 5.8 |
| Asn | 4.5 | 5.9 |
| Thr | 6.1 | 6.5 |
| Ser | 8.3 | 9.6 |
| Glu | 5.7 | 6.3 |
| Gln | 5.7 | 4.0 |
| Pro | 4.5 | 5.5 |
| Gly | 5.7 | 5.6 |
| Ala | 4.8 | 4.4 |
| Val | 5.4 | 5.5 |
| Met | 3.5 | 2.6 |
| Ile | 5.7 | 4.1 |
| Leu | 7.7 | 10.1 |
| Tyr | 4.4 | 3.3 |
| Phe | 5.7 | 4.5 |
| Trp | 2.2 | 1.3 |
| Lys | 5.4 | 6.8 |
| His | 3.5 | 3.2 |
| Arg | 5.0 | 4.2 |

6. Active fragment of human Factor VIII characterized by containing two peptide chains having molecular weights 180,000 daltons and 80,000 daltons, respectively, and having the aminoterminal aminoacid sequences Ala-Thr-Arg-Arg-Tyr-Tyr- and Glu-Ile-Thr-Arg-Thr-Thr-, respectively, and the aminoacid composition:

|  | 80 kD | 180 kD |
|---|---|---|
| Cys | 1.3 | 0.8 |
| Asp | 4.7 | 5.7 |
| Asn | 4.5 | 5.8 |
| Thr | 6.1 | 6.6 |
| Ser | 8.3 | 10.0 |
| Glu | 5.7 | 6.2 |
| Gln | 5.7 | 4.2 |
| Pro | 4.5 | 5.7 |
| Gly | 5.7 | 5.3 |
| Ala | 4.8 | 4.5 |
| Val | 5.4 | 5.3 |
| Met | 3.5 | 2.4 |
| Ile | 5.7 | 4.4 |
| Leu | 7.7 | 10.0 |
| Tyr | 4.4 | 3.2 |
| Phe | 5.7 | 4.4 |
| Trp | 2.2 | 1.2 |
| Lys | 5.4 | 6.9 |
| His | 3.5 | 3.2 |
| Arg | 5.0 | 4.3 |

\* \* \* \* \*

UNITED STATES PATENT AND TRADEMARK OFFICE
CERTIFICATE OF CORRECTION

PATENT NO. : 4,749,780
DATED : June 7, 1988
INVENTOR(S) : Lars-Olof Andersson, et al.

It is certified that error appears in the above-identified patent and that said Letters Patent is hereby corrected as shown below:

Claim 1, line 49 cancel the term "Glu-Ile-Arg-Thr-Thr" and insert --- Glu-Ile-Thr-Arg-Thr-Thr ---.

Claim 3, line 37 cancel the term "Glu-Ile-Arg-Thr-Thr" and insert --- Glu-Ile-Thr-Arg-Thr-Thr ---.

Claim 4, line 63 cancel the term "Glu-Ile-Arg-Thr-Thr" and insert --- Glu-Ile-Thr-Arg-Thr-Thr ---.

Signed and Sealed this

Twenty-seventh Day of November, 1990

Attest:

HARRY F. MANBECK, JR.

*Attesting Officer*  *Commissioner of Patents and Trademarks*